US00RE35421E

United States Patent [19]

Ruiz et al.

[11] E Patent Number: Re. 35,421

[45] Reissued Date of Patent: Jan. 7, 1997

[54] AUTOMATIC CORNEAL SHAPER

[76] Inventors: Luis A. Ruiz, 712 Sawdust Cir., Manakin Sabot, Va. 23103; Sergio Lenchig G., Calle 125 No. 40-28, Int. 22, Bogotá, Colombia

[21] Appl. No.: 280,673

[22] Filed: Jul. 27, 1994

Related U.S. Patent Documents

Reissue of:

[64] Patent No.: 5,133,726
Issued: Jul. 28, 1992
Appl. No.: 479,692
Filed: Feb. 14, 1990

[51] Int. Cl.[6] ..... A61B 17/32

[52] U.S. Cl. ..... 606/166

[58] Field of Search ..... 606/166, 161

[56] References Cited

U.S. PATENT DOCUMENTS

| | | | |
|---|---|---|---|
| 2,480,737 | 8/1949 | Jayle | 606/166 |
| 3,583,403 | 6/1971 | Pohl et al. . | |
| 4,173,980 | 11/1979 | Curtin . | |
| 4,205,682 | 6/1980 | Crock et al. . | |
| 4,429,696 | 2/1984 | Hanna | 606/166 |
| 4,660,556 | 4/1987 | Swinger et al. . | |
| 4,662,370 | 5/1987 | Hoffman et al. . | |
| 4,665,914 | 5/1987 | Tanne . | |
| 4,674,503 | 6/1987 | Peyman et al. . | |
| 4,688,570 | 8/1987 | Kramer et al. . | |
| 4,807,623 | 2/1989 | Lieberman . | |
| 4,884,570 | 12/1989 | Krumeich et al. . | |
| 4,903,695 | 2/1990 | Warner et al. . | |
| 4,997,437 | 3/1991 | Grieshaber . | |
| 5,215,104 | 6/1993 | Steinert | 606/166 X |

OTHER PUBLICATIONS

*Lamellar Refractive Keratoplasty,* Bores Eye Institute 1988, 1989, Chapter 4, pp. 1–9.

Steinway Instrument Company, Inc., *The Steinway/Barraquer In–Situ Microkeratome Set,* Brochure.

*New Methods in Refractive Corneal Surgery—An Experimental Study,* by J. Draeger et al., Klin. Mbl. Augenheilk., 192 (1988), pp. 458–461.

*A Semi–Automatic Electric Keratome for Lamellar Corneal Graft,* by J. Draeger, Klin. Mbl. Augenheilk. 167 (1975) pp. 353–359.

*Primary Examiner*—Michael H. Thaler

*Attorney, Agent, or Firm*—Beveridge, DeGrandi, Weilacher & Young, LLP

[57] ABSTRACT

The invention relates to a mechanical device for performing automatic lamellar corneal resections, in particular, myopic keratomileusis-in-situ and Hyperopic Lamellar Keratotomy. The device includes three major components, a motor and transmission assembly, a shaper head assembly and an eyeball retaining ring. The motor and transmission assembly includes a flexible shaft with a threaded end which is rotated by an electric or turbine motor. The threaded end of the shaft drives a helicoidal pinion on the shaper head assembly which changes the shaft direction by 90°. The shaper head assembly is moved across the rack of the eyeball retaining ring by a series of pinions. The device provides a means for automatically, precisely and safely performing corneal resections.

27 Claims, 9 Drawing Sheets

AUTOMATIC CORNEAL SHAPER

Matter enclosed in heavy brackets [ ] appears in the original patent but forms no part of this reissue specification; matter printed in italics indicates the additions made by reissue.

FIELD OF INVENTION

The present invention is related to medical surgery equipment, particularly to a mechanical device for performing eye surgery, specifically Myopic Keratomileusis-In-Situ and Hyperopic Lamellar Keratotomy. More particularly, the invention is an improvement of such mechanical devices in that it makes the operation of resection completely automatic.

BACKGROUND OF THE INVENTION

The latest technical advances in the medical field include the development over the last 20 years of procedures for operating on the eyes of patients suffering from myopia or hyperopia. Different methods and special instruments have been designed for performing this kind of surgery. One such instrument is a mechanical device bearing a cutting element for performing the operation of resection on the cornea of the eye. There are currently a few of these devices on the market. Known as microkeratomes (MKM), they are suitable for performing Myopic Keratomileusis-In-Situ and Hyperopic Lamellar Keratotomy. In all these devices the cutting element is moved by an electric or turbine motor. This movement is a transverse motion with respect to the direction of the cutting path. It is therefore necessary to push the blade-carrying device manually in order to make the cut. Surgical operations of this kind are presently performed in this manner, and though they have been quite successful, they involve some problems yet to be solved.

To obtain a precise correction of a visual defect, the dimensions of the resection that is made must be very precise. Since resecting is done manually, the precision of the resection depends on factors difficult to control, such as the pressure exerted by the surgeon's hand on the instrument and hence on the patient's eye, or the speed with which he pushes the instrument and its blade to make the resection. The higher the speed, the thinner the section will be, resulting in hypocorrection, and the lower the speed, the thicker the resection will be, resulting in hypercorrection. Moreover, since the sliding parts of the mechanical instrument are finely adjusted, irregular pressure or speed applied by the surgeon to the instrument may cause it to bind. The cutting would then be irregular and would produce irregular astigmatism in the patient's eye. Likewise, irregular pressure on the instrument and on the eye will affect the dimension of the resection.

OBJECTS OF THE INVENTION

One objective of this invention is to provide a mechanical device capable of performing eye surgery, that has a uniform cutting speed minimizing pressure changes on the eye. This device is pushed along by a force of sufficient magnitude evenly distributed so that the resection will be precise and the instrument will not bind along its cutting path.

A second objective is to provide a mechanical instrument capable of performing corneal resections in a completely automatic fashion, so that the "cleanness" of the cut will not be affected by the surgeon's hand.

SUMMARY OF THE INVENTION

This invention consists of an apparatus or device made up of three main parts: a motor and transmission shaft assembly, the shaper head assembly, and a retaining ring assembly. The device is specifically designed to perform corneal resections, which are specialized surgical operations in the medical area of ophthalmology. Automation of the device includes making the shaper head assembly move automatically and smoothly at a constant speed across the retaining ring assembly, which holds the eye in position for resection. The function of the motor and transmission shaft assembly is to impart and transmit a uniform mechanical motion, by a means of transmission, both to the cutting blade in the shaper head assembly and to the shaper head assembly. The transmission *means* causes said *blade* to oscillate transversally at a constant rate, and it causes the shaper head assembly to move longitudinally, smoothly and at a constant speed across the retaining ring assembly and thus across the cornea, therein making the desired resection.

For a better understanding of the invention, a detailed explanation of the same is given below with reference made to the attached drawings.

DETAILED DESCRIPTION OF PREFERRED EMBODIMENT

A description is given in this section, which reference to the attached drawings, of the mechanical device of this invention, which is capable of performing eye surgery of the resection type shaping, or myopic and Hiperopic shaping.

Figure 1:
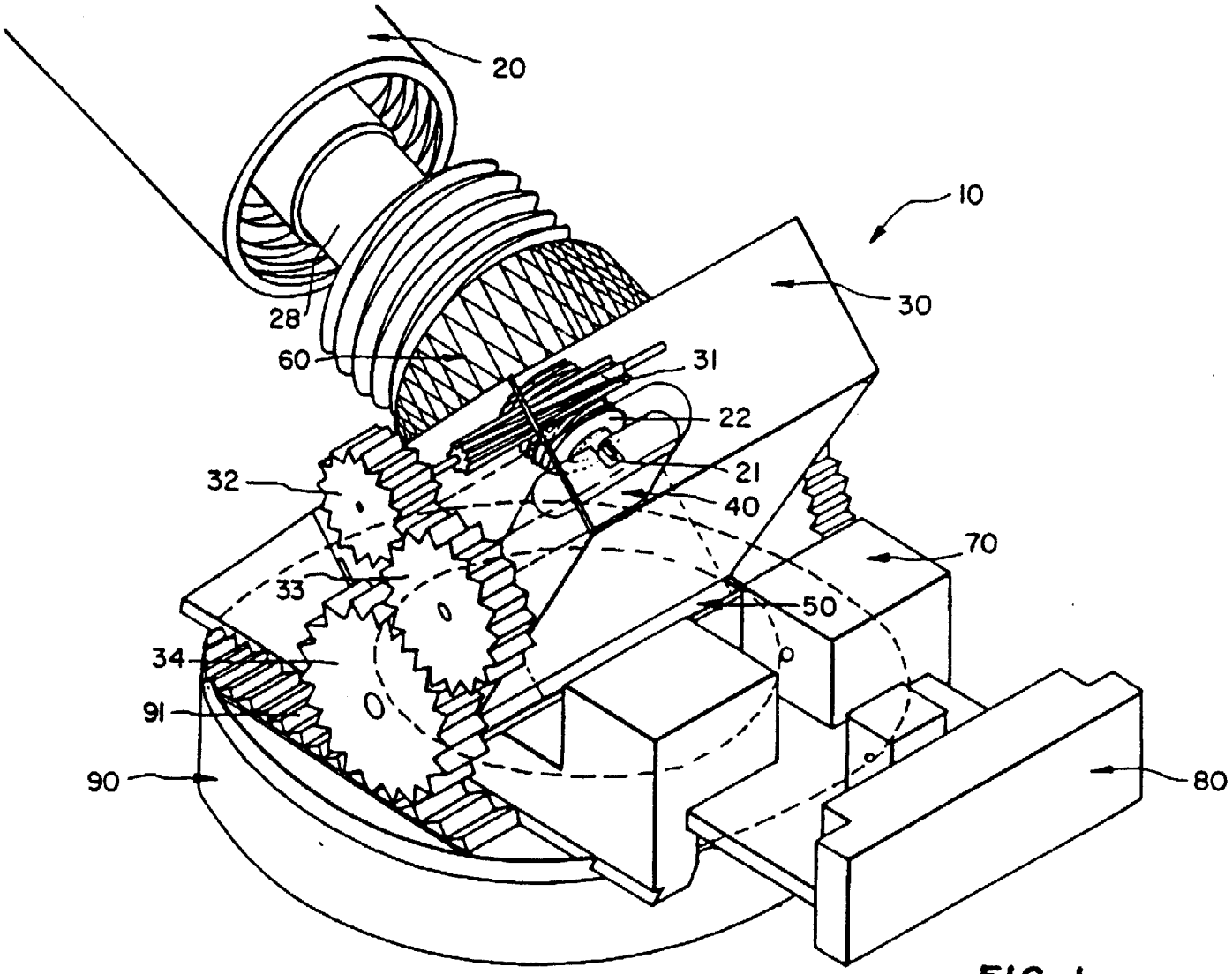
FIG. 1 is a perspective view of the mechanical device of this invention.

The mechanical device 10, specifically designed to perform surgical operations on eyes to correct for myopia and hyperopia, is shown in perspective, as a complete unit, in FIG. 1. The device is drawn in said FIG. 1 as though it were transparent, to reveal several of its essential internal parts.

Said mechanical device 10 is basically made up of the following main component parts.

The motor and transmission shaft assembly 20, the figure shows only the end of the transmission shaft that fits into the upper body 30, this end of the shaft being the only part of said assembly of interest to this invention. No description will be given of the motor and the rest of the shaft because they are well-known elements of the prior art and do not form part of this invention.

Figure 5B:
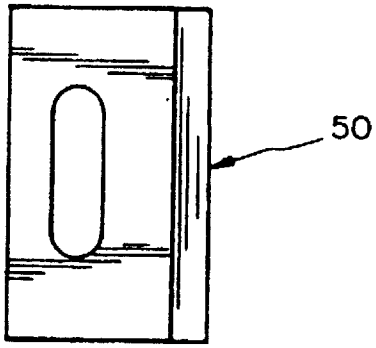
FIGS. 5, 5A and 5B are the front, lateral and top views of the cutting element or blade.
Figure 5A:
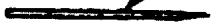
Figure 5:
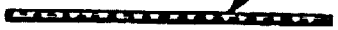

An upper body 30, which comprises a means of transmitting motion to the cutting element 50 (see also FIGS. 5, 5A and 5B).

A sliding skate 70, to which the upper body 30 is immovably fitted, and which in turn is fitted onto the fixation ring 90 in such a way as to be free to slide across it.

A plate 80, which slides into said skate 70 up to a predetermined fixed position. Said plate 80 defines the thickness of the resection.

A fastening nut 60, whose function is to hold the upper body 30 and said sliding plane 70 immovably joined together, these two parts together forming the shaper head.

A retaining ring assembly 90, whose function in the apparatus as a whole is to fix the eye in position and at the same time to provide a fixed support along which the shaper head will slide to resect the corneal disc with the blade 50. The blade 50 is fitted into the blade holder 40, which in turn *is* inserted into said upper body of the shaper head. This retaining ring is able to work with or without vaccum or with pressure only.

Following the above general identification of the main parts of said mechanical device 10, a detailed description is given below of each one of them to explain how the device works and thus make clear the object and scope of this invention.

Figure 2B:
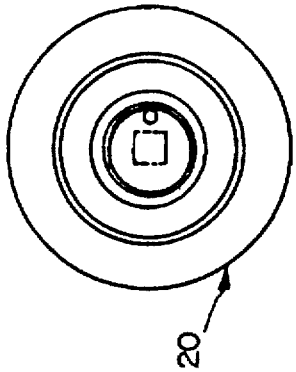
FIGS. 2, 2A and 2B are the top view, longitudinal section, and front view, respectively, of one end of the transmission shaft.
Figure 2A:
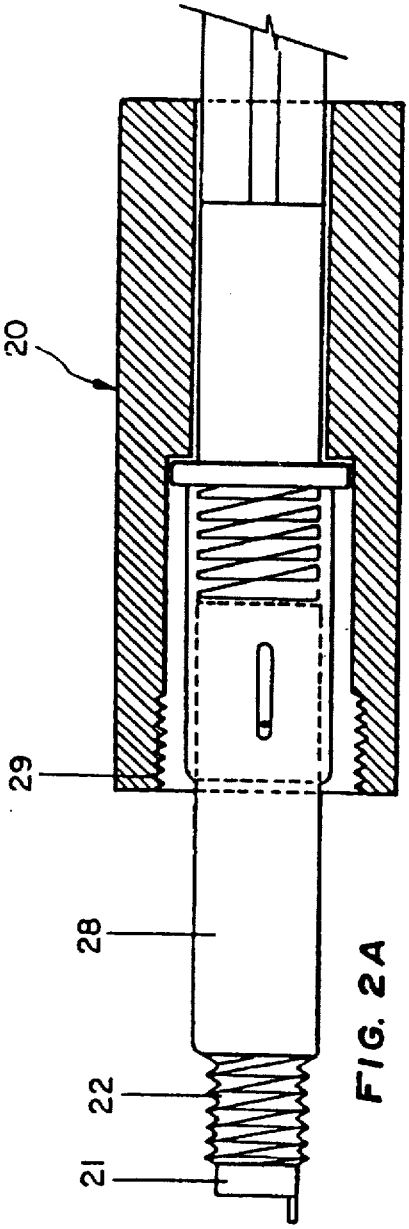
Figure 2:
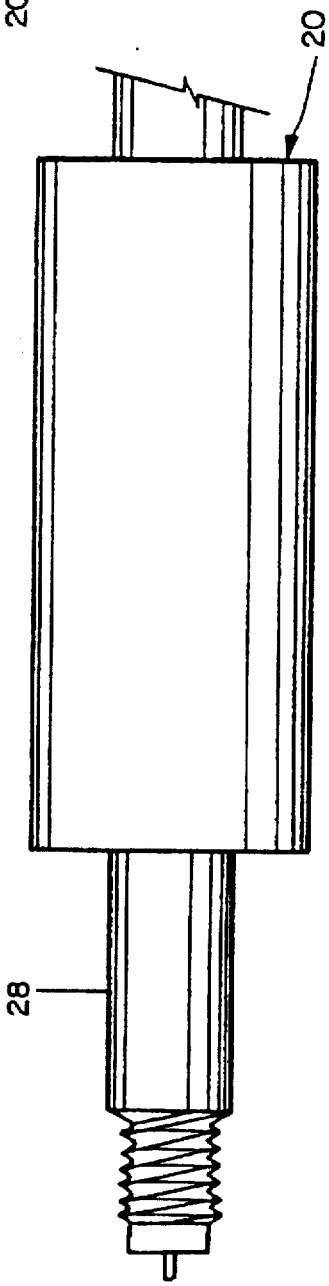

FIGS. 2, 2A and 2B show the end of the transmission shaft of the motor and transmission shaft assembly 20. At the extreme end of the shaft end 28 there is a threaded area 22 working as an endless pinion, and at the very tip projects a small spindle that is parallel to but not concentric with said shaft 28; this spindle will hereafter be referred to as the eccentric 21. No description will be given of the other parts of the transmission shaft, for they are well known parts in the [ant] *art* of flexible shafts; such parts include jacket 29 and other components. Said shaft end 28 is introduced through a hole in the threaded area 35 (see FIGS. 3A and 3B) of the upper body 30 (see FIG. 1) and moved further into said body. Once said shaft point 28 is in place it becomes mechanically connected in its threaded area 22 to a pinion-shaft 31 (see, FIG. 1) that changes the direction of the axis of rotation by 90° with respect to the transmission shaft 20. Rotation is imparted to said pinion-shaft 31 upon mutual engagement of the two, that is the threaded area 22 of the transmission shaft and the threaded area of the pinion-shaft 31. The eccentric 21 fits into a vertical slot along the body of the blade holder 40. An oscillating motion is imparted to said blade holder 40 by the eccentric 21 as the eccentric revolves with the transmission shaft. (See FIG. 1).

Figure 3A:
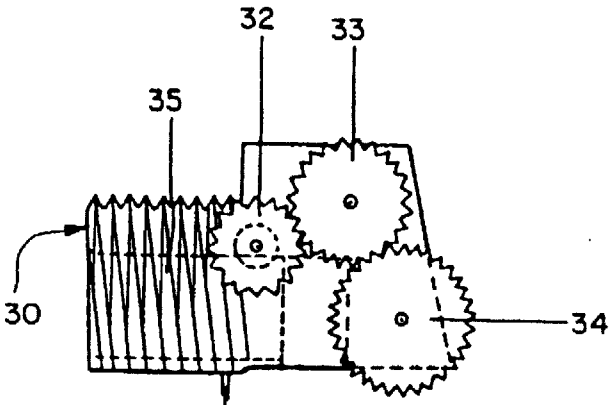
FIGS. 3, 3A and 3B are the front, lateral and bottom elevations of the pinion-bearing upper body of the shaper head assembly.
Figure 3:
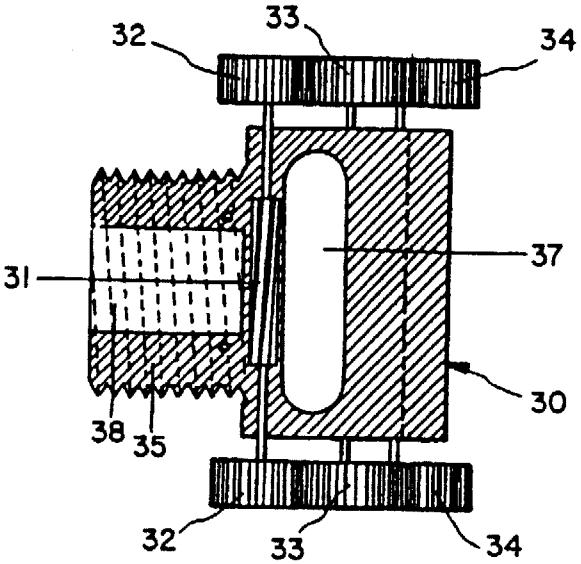
Figure 3B:
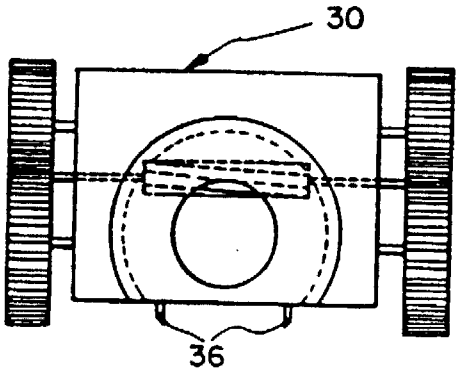
Figure 6B:
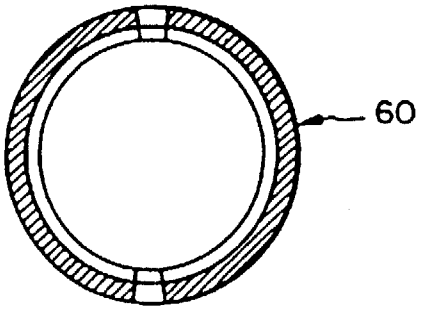
FIGS. 6, 6A and 6B are the lateral elevation, cross section, and bottom elevation of the nut that fastens together the upper pinion-bearing body and the sliding skate of the shaper head assembly.
Figure 6A:
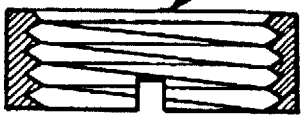
Figure 6:
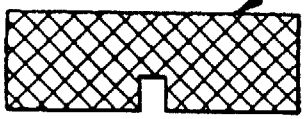

Said upper body 30 is shown in detail in FIGS. 3, 3A, and 3B, and is manufactured out of surgical-grade stainless steel. Said upper body has a cylindrical threaded area 35 that is cut straight on the underside and has a cylindrical hole through which is inserted the shaft end 28 referred to above; a pinion-shaft 31, which engages to said threaded area 22 of said shaft end 28, said pinion shaft 31 runs through said upper body, juts out of the opposite lateral walls of said body, and is connected at each end to a pinion 32. In each one of said lateral walls of said upper body there are two forced in-shafts fitted with pinions 33 and 34, pinion 33 being engaged with pinion 32 and being larger in diameter, while pinion 34 being engaged with pinion 33 and being in turn larger in diameter. The relationship between the diameters of the set of pinions being chosen according to the required blade advancing speed. Toward the central part of the upper body, on the underside, there is a cavity 37 with a rectangular section and rounded ends. The blade holder 40 fits into this cavity 37. On the straight-cut part of the threaded area 35, toward the beginning of the thread on the body, there are two protruding pins 36 whose function will be understood from the description of the sliding skate 70 given below.

Figure 4B:
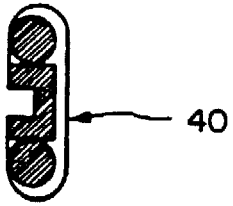
FIGS. 4, 4A and 4B are the front, lateral and top elevations of the blade holder.
Figure 4A:
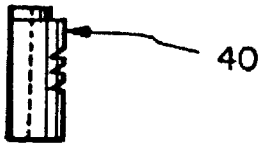
Figure 4:
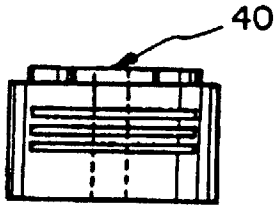

FIGS. 4, 4A and 4B show the blade holder 40, which has the shape of a rectangular parallelepiped with rounded corners, comprising on one of its wider faces three horizontal, triangular wedge-shaped slots. On the opposite side, the vertical slot referred to above is located. This is the vertical slot into which the eccentric 21 will be inserted to impart the transverse oscillatory motion to said blade holder 40. On the top side of the blade holder (see FIGS. 4 and 4B) there is a boss shaped like an inverted "C" in the center, with two circles above and below the "C " (see hatched area in FIG. 4B).

The function of said boss is to receive the blade 50 shown in FIGS. 5, 5A and 5B. Toward the center of said blade there is an essentially rectangular-shaped hole with rounded ends that fits perfectly onto the boss of the blade holder 40. Said blade holder is then introduced into said cavity 37 in the upper body 30 in such a way that the blade is held parallel to the underside of the upper body 30.

Figure 7B:
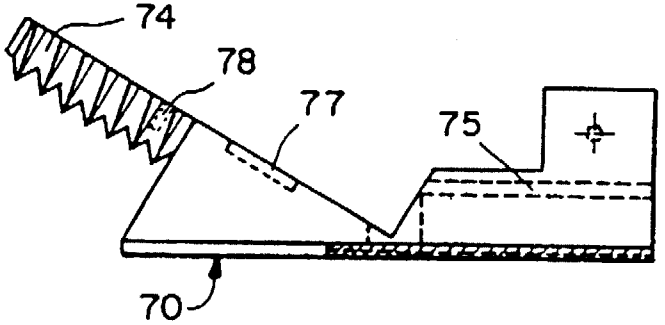
FIG. 7, 7A and 7B are the front, top and lateral elevations of the sliding skate.
Figure 7A:
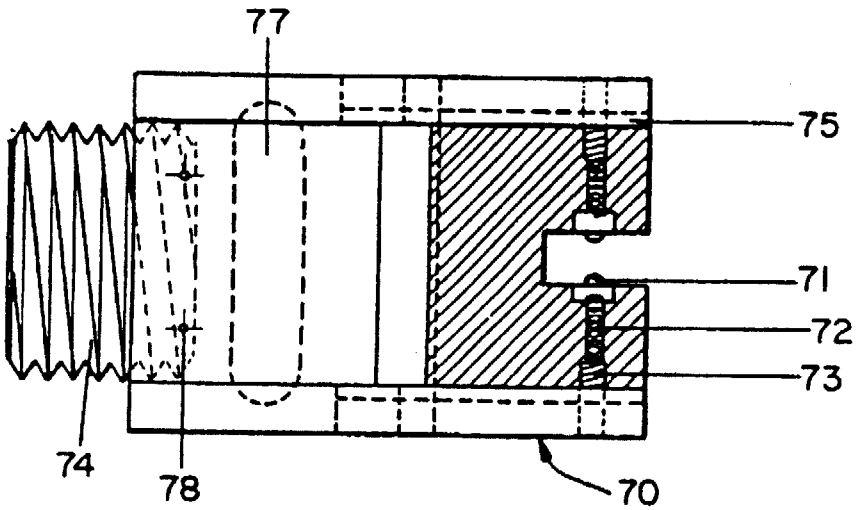
Figure 7:
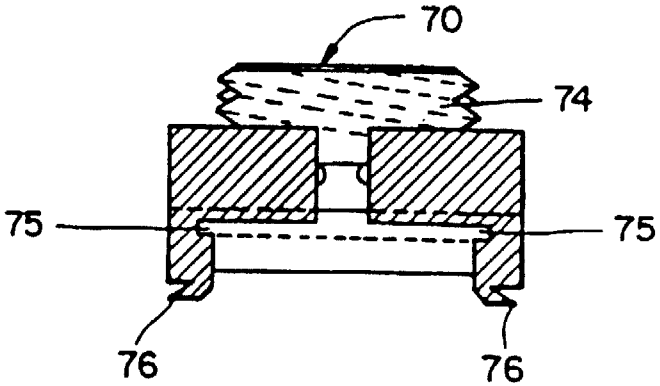

Said upper body 30 is then joined to the sliding skate 70 shown in FIGS. 7, 7A and 7B. The sliding [plane] *skate* 70 has a threaded area 74 which has a straight cut and which follows and inclined plane with respect to the plane formed by the dovetails 76. On said plane there is a rectangular-shaped recess 77 with rounded ends like cavity 37 in the upper body 30. Said upper body 30, with all its elements described above duly assembled, is so placed that the cut face of the threaded area 35 coincides with the cut face of the threaded area 74 of the sliding skate 70. In this way the two pins 36 on the body 30 are inserted into the two holes 78 provided in the sliding skate, and the blade holder 40 coincides with the recess 77 so that the cutting element 50 becomes duly secured. Then the two parts, the upper body 30 and the sliding skate 70, are fixed together as a single unit by screwing on the fastening nut 60 over the thread formed by the threaded parts 35 and 74. The blade is thus in the proper position for making a resection; although free to move transversally because the length of the cavity 37 in the upper body 30 is somewhat greater than the length of the blade holder 40.

Figure 8B:
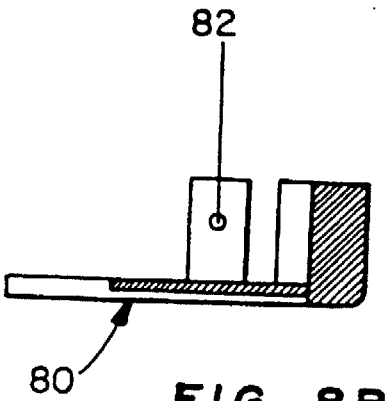
FIGS. 8, 8A and 8B are the front, top and lateral elevations of the plate, whose thickness determines the thickness of resection.
Figure 8A:
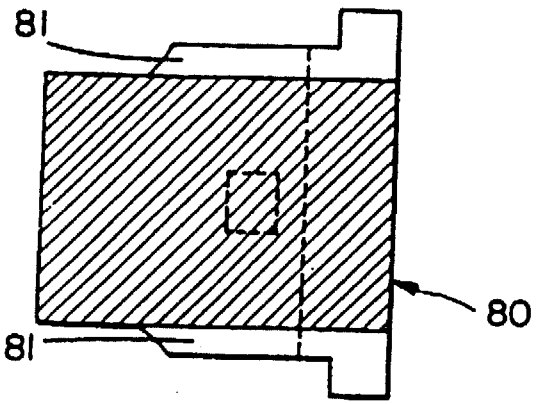
Figure 8:
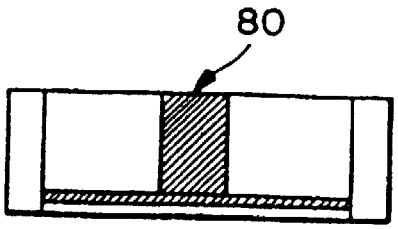

With reference again to FIGS. 7, 7A and 7B, two parallel slots 75 can be seen above a rectangular-shaped opening in the body of the sliding skate 70. Plate 80 is inserted into said opening in a sliding manner along said slots 75 (see FIG. 1). The thickness of the plate determines the depth of resection, thus a resection of predetermined depth can be made by using a plate of appropriate thickness. FIGS. 8, 8A and 8B show the general form of plate 80. FIG. 8B highlights a part of the plate that is shaped like a rectangular parallelepiped and has two circular holes 82. These holes serve to retain plate 80 in position in the sliding skate 70 when the holes fit over the spheres 71 located in the body of the sliding skate 70. The springs 72, which are held in place by the screws 73, keep said spheres pressed outward.

All the parts described above make up the mobile means of the mechanical device once they are assembled together. This mobile means is the cutting instrument. (See FIG. 10).

Figure 9:
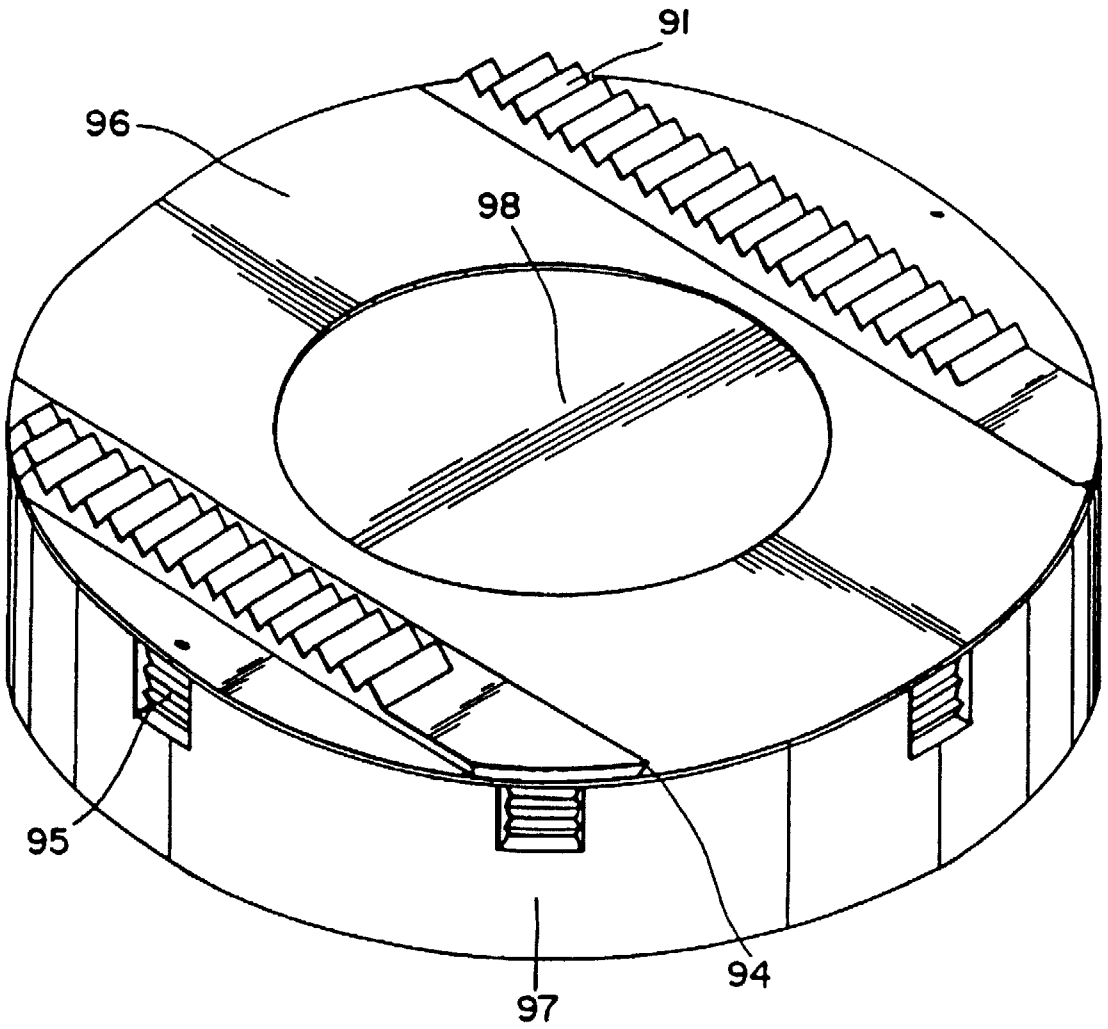
FIG. 9 is a perspective view of the retaining ring assembly of this invention.
Figures 9A, 9B, 9C, 9D, 9E, 9F, 9G, 9H, 9J:
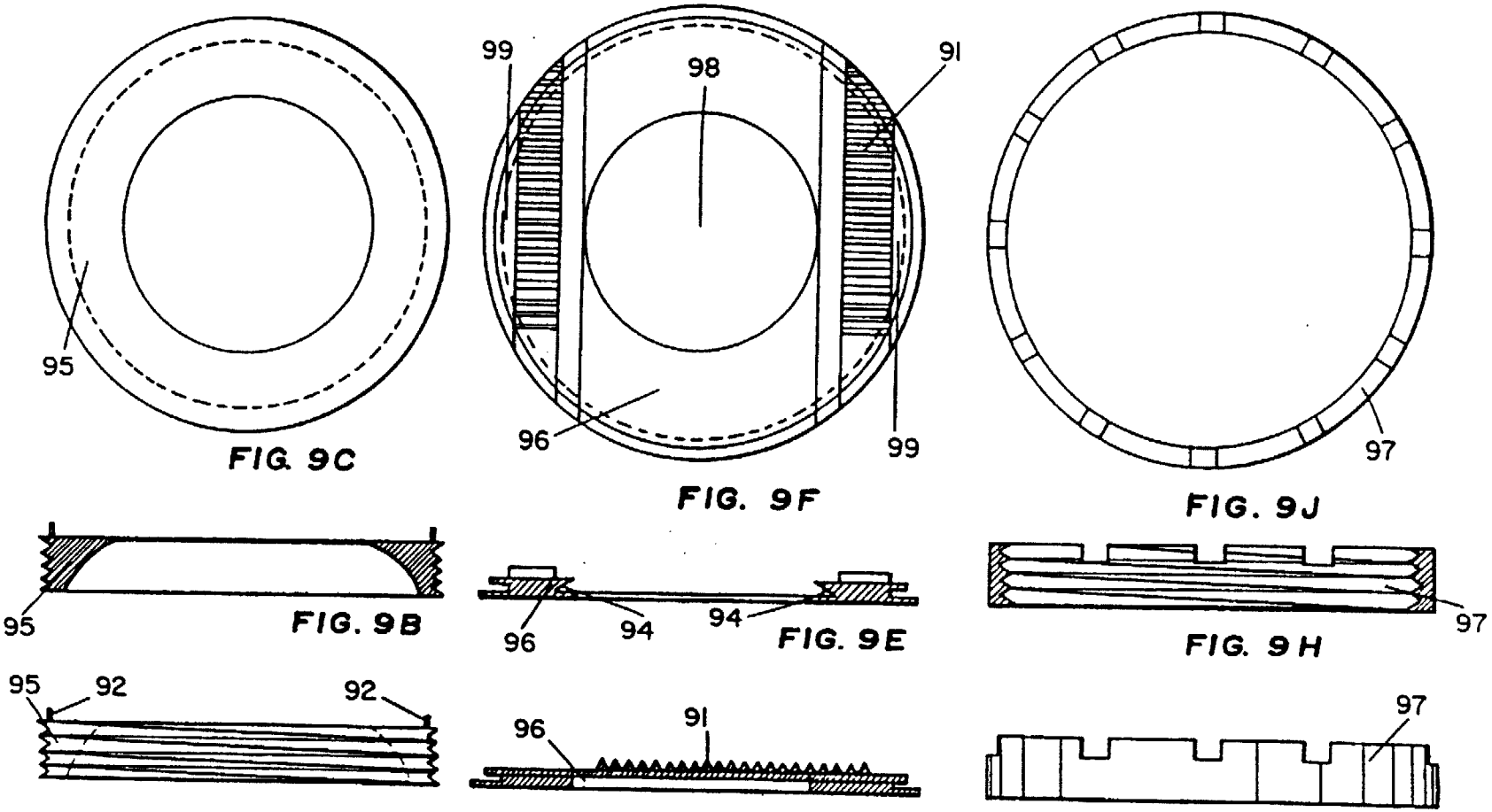
FIGS. 9A, 9B, 9C, 9D, 9E, 9F, 9G, 9H and 9J show the component parts of the retaining ring assembly of FIG. 9.

The fixed part or support of the mechanical device is the retaining ring assembly 90, which is shown in FIG. 9. As can be seen, it is circular in shape and has a circular concentric hole 98. When said retaining ring assembly 90 is placed over the patient's eyeball, the cornea will appear centered on said hole 98 and protruding through it. FIGS. 9D, 9E and 9F show an upper ring 96 with two parallel toothed tracks 91 on it which run across ring 90 along the sides of hole 98. FIG. 9E shows two V-shaped grooves 94 that run parallel to the tracks 91. The dovetails 76 of the sliding skate 70 (see FIG. 7) are inserted into these grooves 94 in such a way that each one of the tracks 91 engages one of the pinions 34 of the upper body 30.

With reference again to FIG. 9, a description is given below of the retaining ring assembly 90, which comprises three components:

A slender upper ring 96 that has the hole 98, the tracks 91, the grooves 94 and two small holes 99 (see FIGS. 9D, 9E and 9F).

An inner ring 95 that has an outer thread and two pins 92 which will be inserted into the holes 99 in the upper ring 96. The inside of said ring 95 is shaped like a circular seat in which the patient's eyeball will be adjusted (see FIGS. 9A, 9B and 9C).

An outer ring 97 with an inner thread that serves to hold together the two preceding rings, the three together forming the complete eye retaining ring assembly (see FIGS. 9G, 9H and 9J).

The apparatus is thus ready to fulfill its purpose of resecting the cornea of the patient's eye.

Next, the transmission shaft is connected by inserting the shaft end 28 (FIGS. 2 and 2A) through hole 38 in the upper body 30 until the eccentric 21 enters the vertical slot of the blade holder 40 and the threaded area 22 of the shaft end 28 engages the pinion shaft 31 (see FIGS. 3, 3A, 4B and 1).

Figure 10:
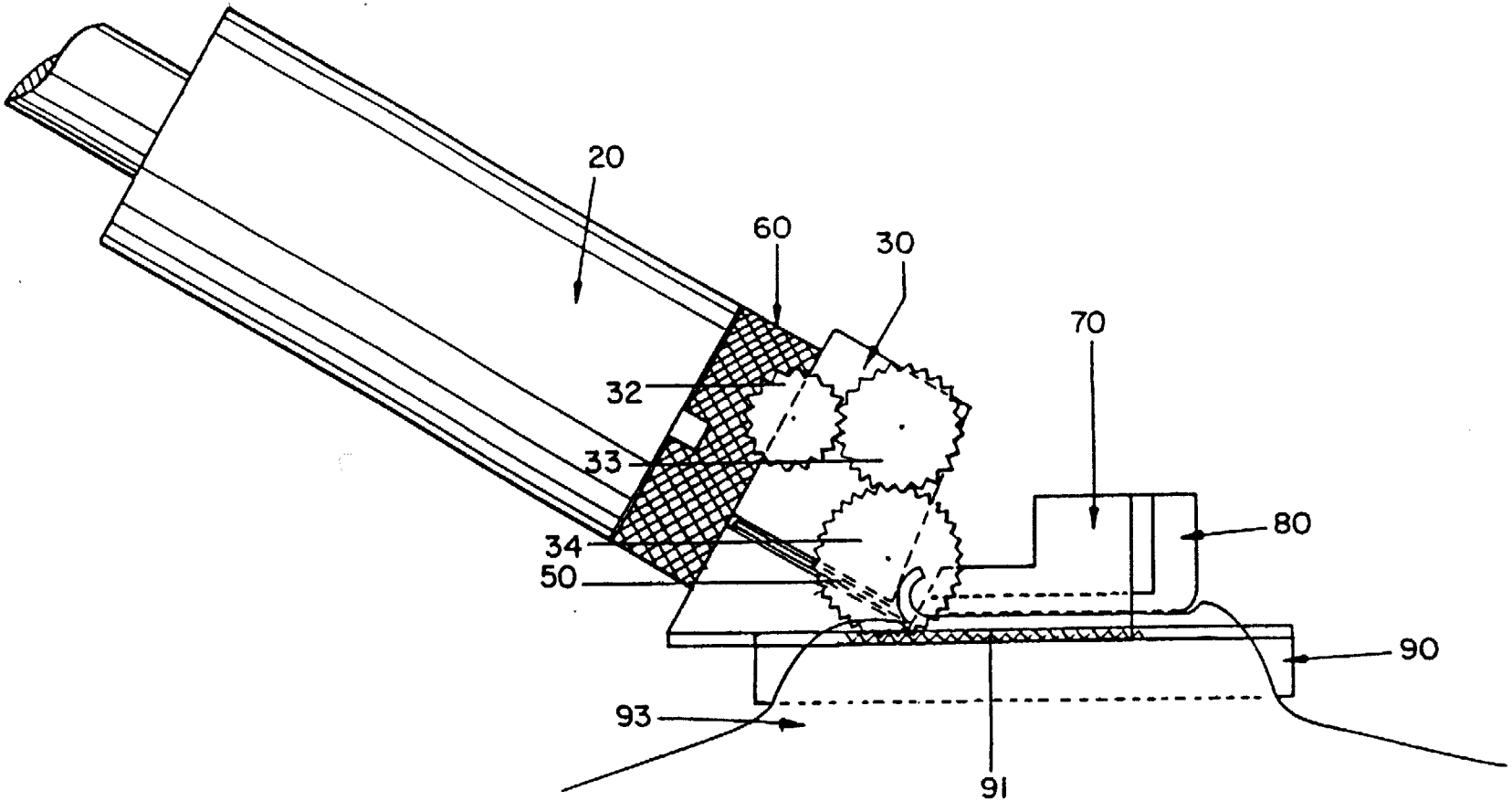
FIG. 10 is a sketch of the mechanical device in the process of performing a corneal resection on an eye.

It only remains now to start the motor for the resection to be made automatically, precisely and safely (see FIG. 10). The high degree of resecting precision obtained in this way ensures that the patient under treatment will receive the required visual correction.

It is to be understood that the above description of the invention is made to exemplify the preferred embodiment and in no way limits the scope of this invention. One skilled in the art will realize that it is possible to make modifications or variations without departing from the spirit or scope of this invention.

We claim:

1. An automatic mechanical device for performing lamellar corneal resections comprising:

a driving means, a mobile means connected to said driving means, said mobile means including a cutting means for performing corneal resections, an eyeball retaining means [movably] connected to said mobile means so that the *mobile means is moveable with respect to said eyeball retaining means and so that the* resection can be made with precision, and a transmission means connected to said driving means to provide simultaneous lineal and transverse oscillatory motion to said cutting means to automate lineal and transverse driving of the cutting means during the resecting operation, wherein the driving means comprises an electric or turbine motor and said transmission means includes a flexible transmission shaft, said flexible transmission shaft including a shaft point that connects to said mobile means, said shaft point having a threaded area forming an endless pinion, and a tip of said shaft point being provided with an eccentric, said threaded area transmitting lineal motion to said mobile means, and said eccentric transmitting transverse oscillatory motion to said cutting means in a direction perpendicular to said linear motion.

2. An automatic mechanical device for performing lamellar corneal resections comprising:

a driving means, a mobile means connected to said driving means, said mobile means including a cutting means for performing corneal resections, an eyeball retaining means [movably] connected to said mobile means so that the *mobile means is moveable with respect to said eyeball retaining means and so that the* resection can be made with precision, and a transmission means connected to said driving means to provide motion to said cutting means to automate the resecting operation, wherein said mobile means comprises an upper body carrying said transmission means, said upper body having a cylindrical threaded area, cut straight on the underside, a cylindrical hole through said cylindrical threaded area into which a shaft point of said transmission shaft is introduced, an essentially rectangular-shaped cavity whose shorter sides are curved, wherein two pins project from the straight-cut part of said threaded cylindrical area; a sliding skate on which said upper body with said cutting means is mounted, said sliding skate including a sliding skate threaded area, with a straight cut that follows an inclined plane with respect to a base of said sliding skate, a recess with a transverse section identical to said cavity of said upper body, said base being formed by dovetail tracks along the length of said sliding skate and a rectangular-shaped opening having at the top two parallel rectangular grooves along the length of said sliding skate, two small holes in the straight-cut part of said threaded area which receive said pins of the threaded area of said upper body; a nut that screws on over the complete thread formed by the threaded areas when the upper body is mounted on the sliding skate; a plate that slides in through said opening and along said two grooves, said plate having a boss shaped like a rectangular parallelepiped with two holes in the side walls that fit together with the fixing means in the sliding skate; said fixing means including two screws, two springs and two balls protruding from the linear side walls of said opening in said sliding skate.

3. The automatic mechanical device of claim 2, wherein said transmission means includes a pinion-shaft that engages said threaded area of said shaft end of said transmission shaft changing the direction of the axis of rotation, said pinion-shaft running through said upper body and protruding at each end through opposite side walls of said upper body; two first pinions directly connected, one to each end of said pinion shaft; two first shafts forced in said side walls and bearing at their free ends two second pinions mechanically coupled with said first pinions; two second shafts forced in said side walls and bearing at their free ends two third pinions mechanically coupled with said second pinions.

4. The automatic mechanical device of claim 3, wherein said eyeball retaining means includes a circular retaining ring assembly with a central hole which is concentric with the outer edge of the ring and which accommodates the cornea of the patient undergoing surgery, said retaining ring including an upper ring with two parallel toothed tracks which engage said two third pinions of said transmission means and on which said mobile means will move during the resection procedure, taking said cutting means across the cornea, wherein said eyeball retaining means further includes an inner ring threaded on the outside and an outer ring threaded on the inside to set and screw said outer ring onto said inner ring.

5. The automatic mechanical device of claim 2, wherein said cutting means includes a blade holder having a rectangular parallelepiped shape with rounded corners, three horizontal slots in one of its broad faces, a vertical slot in a face opposite to the face with said three slots, said vertical slot receiving said eccentric of said shaft end to impart transverse oscillatory motion to said cutting means, a boss that is C-shaped in the center with two circles, one above and one below the C; an essentially rectangular shaped blade made of surgical stainless steel with the cutting edge along one of its longer sides and with a hole on the inside that is essentially rectangular in shape, wherein the smaller opposite sides of the essentially rectangular hole are curved and match said boss of said blade holder; said blade holder and said blade being fitted together and inserted in said cavity of said upper body.

6. An automatic mechanical device for performing lamellar corneal resections comprising:

a driving means, a mobile means connected to said driving means, said mobile means including a cutting means for performing corneal resections, an eyeball retaining means [movably] connected to said mobile means so that the *mobile means is moveable with respect to said eyeball retaining means and so that the* resection can be made with precision, and a transmission means connected to said driving means to provide simultaneous lineal and transverse oscillatory motion to said cutting means to automate lineal and transverse driving of the cutting means during the resecting operation, wherein said eyeball retaining means includes a circular retaining ring assembly with a central hole which is concentric with the outer edge of the ring and which accommodates the cornea of the patient undergoing surgery, said retaining ring including an upper ring with two parallel toothed tracks which engage a pair of pinions of said transmission means and on which said mobile means will move during the resection procedure, taking said cutting means across the cornea, and wherein said eyeball retaining means includes an inner ring threaded on the outside and an outer ring threaded on the inside.

7. An automatic mechanical device for performing lamellar corneal resections comprising:

a driving means, a mobile means connected to said driving means, said mobile means including a cutting means for performing corneal resections, an eyeball retaining means [movably] connected to said mobile means so that the *mobile means is moveable with respect to said eyeball retaining means and so that the* resection can be made with precision, and a transmission means connected to said driving means to provide simultaneous lineal and transverse oscillatory motion to said cutting means to automate lineal and transverse driving of the cutting means during the resecting operation, wherein the driving means comprises an electric or turbine motor and said transmission means includes a transmission shaft, said transmission shaft including a shaft point that connects to said mobile means, said shaft point having a threaded area forming an endless pinion, and a tip of said shaft point being provided with an eccentric, said threaded area transmitting lineal motion to said mobile means, and said eccentric transmitting transverse oscillatory motion to said cutting means in a direction perpendicular to said linear motion.

8. An automatic mechanical device for performing lamellar corneal resections, comprising:

a driving means, a mobile means connected to said driving means, said mobile means including a cutting means for performing corneal resections, an eyeball retaining means [movably] connected to said mobile means so that the *mobile means is moveable with respect to said eyeball retaining means and so that the* resection can be made with precision, and a transmission means connected to said driving means to provide simultaneous lineal and transverse oscillatory motion to said cutting means to automate lineal and transverse driving of the cutting means during the resecting operation, wherein said eyeball retaining means includes a circular retaining ring assembly with a central hole which is concentric with the outer edge of the ring and which accommodates the cornea of the patient undergoing surgery, said retaining ring including an upper ring with at least one toothed track which engages at least one pinion of said transmission means and on which said mobile means will move during the resection procedure, taking said cutting means across the cornea, and wherein said eyeball retaining means includes an inner ring threaded on the outside and an outer ring threaded on the inside.

*9. A device as recited in claim 1 wherein said transmission means includes a first component in driving engagement with the threaded area of said shaft point and directly supported by said mobile body, and said transmission means further comprising a second component located directly at said eyeball retaining means.*

*10. A device as recited in claim 7 wherein said transmission means includes a first component in driving engagement with the threaded area of said shaft point and directly supported by said mobile body, and said transmission means further comprising a second component located directly at said eyeball retaining means.*

*11. An automatic microkeratome device for performing lamellar corneal resections comprising:*

*an eyeball retainer including an aperture through which a portion of the cornea is exposed, a guideway defining a linear path, and a first drive element;*

*a mobile body movably mounted on said eyeball retainer, said mobile body including at lease one follower element engaging said guideway to guide said mobile body along said linear path and across said aperture;*

*a blade mounted to said mobile body for movement therewith along said linear path, said blade having a*

*cutting edge extending outward from said mobile body for resecting a portion of said cornea as said mobile body moves across said aperture;*

*a plate member including a bottom face extending forwardly beyond said cutting edge of said blade to contact said cornea prior to said cutting edge, said cutting edge being spaced downward relative to said bottom face of said plate member such that a vertical space is defined therebetween, said defined vertical space setting the depth of the corneal resection;*

*a second drive element attached to said mobile body and in engagement with said first drive element;*

*a power source; and*

*a transmission coupling operatively coupling said power source to said first and second drive elements to cause relative movement between said first and second drive elements to thereby move said mobile body along said linear path so that said blade resects a lamellar portion of the cornea.*

*12. An automatic microkeratome device in accordance with claim 11 in which said first drive element includes at least one linear toothed rack fixed along a top surface of said eyeball retainer, and said second drive element includes at least one pinion rotatably mounted to said mobile body and engaged with said toothed rack.*

*13. An automatic microkeratome device in accordance with claim 11 in which said guideway includes at least one dovetail shaped rail and said follower includes at least one dovetail shaped runner in engagement with said rail.*

*14. An automatic microkeratome device in accordance with claim 11 in which said blade is mounted for lateral reciprocating movement relative to said mobile body, and in which said transmission coupling operatively couples said power source to said blade to effect said lateral reciprocating movement of said blade.*

*15. An automatic microkeratome device in accordance with claim 11 in which said blade is inclined relative to the direction of motion of said mobile body along said linear path.*

*16. An automatic microkeratome device in accordance with claim 11 in which said power source is an electric motor.*

*17. An automatic microkeratome device in accordance with claim 11 in which said power source is a turbine motor.*

*18. An automatic microkeratome device for performing lamellar corneal resections comprising:*

*a driving means;*

*a mobile means connected to said driving means, said mobile means including a cutting means for performing corneal resections, guide elements, and a drive member;*

*an eyeball retaining means connected to said mobile means so that the mobile means is moveable with respect to said eyeball retaining means and so that the resection can be made with precision, said eyeball retaining means including an aperture through which a portion of the cornea to be resected is exposed, linear guideways connected to said guide elements to guide said mobile means along a path for resecting the cornea, and a drive element movably connected to said drive member;*

*a plate member connected to said mobile means for movement therewith, said plate member including a lower surface spaced from said cutting means to engage at least part of the exposed cornea and define the depth of the resection;*

*a transmission means connected to said driving means to provide simultaneous lineal and transverse motion to said cutting means to automate lineal and transverse driving of said cutting means during the resecting operation, said transmission means being connected to said drive member to cause relative movement between said drive member and said drive element to cause said mobile means to automatically move across said guideways of said eyeball retaining means at a substantially uniform rate, and said transmission means being connected to said cutting means to move said cutting means transversely relative to said mobile means.*

*19. An automatic mechanical device for performing lamellar corneal resections, comprising:*

*a first transmission sub-assembly which includes a driving shaft with fitting end;*

*a mobile body which supports the fitting end of said driving shaft such that said fitting end is free to rotate;*

*a cutting member;*

*a cutting member support to which said cutting member is fixed, said cutting member support being supported by said mobile body such that said cutting member support is free to oscillate with respect to said mobile body, and said cutting member support being in driving engagement with said driving shaft with said driving engagement producing an oscillating motion in said cutting member support and cutting member when said fitting end rotates;*

*an eye retaining member which includes an aperture through which a cornea to be operated upon extends through, and said mobile body being slidingly received by said retaining member;*

*a second transmission sub-assembly including a first component in driving engagement with the fitting end of said driving shaft and directly supported by said mobile body, said second transmission sub-assembly further comprising a second component located directly at said retaining member, and said second transmission sub-assembly being arranged such that rotation of said driving shaft conveys a driving force to said first component which is in driving communication with said second component at said retaining member such that said mobile body slides with respect to said retaining member and such that the cutting member passes over the aperture formed in said retaining member, and wherein the driving of said driving shaft results in a simultaneous oscillation of said cutting member and sliding of said mobile body with respect to said retaining member.*

*20. A device as recited in claim 19, wherein said fitting end of said driving shaft includes an endless pinion, and said first component is a pinion shaft rotatably fixed with respect to said mobile body, and said second component is a first side rack fixed to said retaining member, and said second transmission sub-assembly further including at least one pinion member which receives a driving force from said pinion shaft, is rotatably supported by said mobile body and is in contact with said first side rack.*

*21. A device as recited in claim 20 wherein said pinion shaft includes two ends extending to opposite sides of said mobile body with a first pinion member and a second pinion member fixed to said ends, said second transmission sub-assembly further comprising a second side rack positioned on an opposite side of said mobile body as said first side rack, and said first pinion member being in driving communication with said first side rack and said second pinion*

*member being in driving communication with said second side rack.*

*22. A device as recited in claim 19 wherein said second transmission sub-assembly includes a plurality of different sized pinion members on each side of said mobile body each rotatably supported by said mobile body.*

*23. A device as recited in claim 19 wherein said mobile body includes a sliding skate and an upper body portion removably secured to said sliding skate, said sliding skate having side edges in sliding engagement with corresponding side recesses formed in said eye retaining member, and said upper body including a hole which receives the fitting end of said driving shaft, and said driving shaft further including an eccentric pin extending out from said fitting end and into engagement with said cutting member support, and said cutting member support being received within a slot formed in said upper body portion.*

*24. A device as recited in claim 19 further comprising a lamellar corneal resection defining plate slidingly received by said mobile body so as to present a planar surface a distance above the aperture formed in said eye retaining member, and said mobile body including means to releasably secure said sliding plate with respect to said mobile body.*

*25. A device as recited in claim 19 wherein said mobile body is restricted by said eye retaining member to sliding travel along a first linear direction and said blade oscillates in a direction transverse to said first linear direction.*

*26. An automatic mechanical device for performing lamellar corneal resections, comprising:*

*a first transmission sub-assembly which includes a driving component with a coupling end;*

*a mobile body which supports the coupling end of said driving component of said first transmission sub-assembly;*

*a cutting blade;*

*a blade support to which said cutting blade is fixed, said blade support being supported by said mobile body such that said blade support is free to oscillate with respect to said mobile body, and said blade support being in driving communication with said driving component of said first transmission sub-assembly such that an oscillating motion in said blade is produced when said first transmission sub-assembly is operating;*

*an eye retaining member which includes an aperture through which a cornea to be operated upon extends through, and said mobile body being slidingly received by said eye retaining member;*

*a second transmission sub-assembly in driving engagement with said first transmission sub-assembly, said second transmission sub-assembly including a first component directly supported by said mobile body and a second component located directly on said retaining member, and said second transmission sub-assembly being directly engaged with said eye retaining member such that said second transmission sub-assembly pulls said driving component of said first transmission sub-assembly forward as said second transmission sub-assembly slides said mobile body with respect to said eye retaining member.*

*27. A device as recited in claim 26 wherein said driving component is a shaft rotatably supported by said mobile body, and said second transmission sub-assembly is positioned forward, with respect to a lineal travel direction of said cutting blade, of the coupling end of said shaft such that said second transmission sub-assembly pulls said shaft forward across said eye retaining member.*

* * * * *